(12) United States Patent
Rodriguez et al.

(10) Patent No.: US 10,314,575 B2
(45) Date of Patent: Jun. 11, 2019

(54) SUTURE FIXATION DEVICE AND METHOD THEREOF

(71) Applicant: Hospital for Special Surgery, New York, NY (US)

(72) Inventors: William Rodriguez, Garfield, NJ (US); Riley J. Williams, New York, NY (US)

(73) Assignee: Hospital for Special Surgery, New York, NY (US)

( * ) Notice: Subject to any disclaimer, the term of this patent is extended or adjusted under 35 U.S.C. 154(b) by 240 days.

(21) Appl. No.: 15/235,413

(22) Filed: Aug. 12, 2016

(65) Prior Publication Data

US 2017/0042536 A1 Feb. 16, 2017

Related U.S. Application Data

(60) Provisional application No. 62/204,027, filed on Aug. 12, 2015.

(51) Int. Cl.
*A61B 17/06* (2006.01)
*A61B 17/04* (2006.01)
*A61B 17/00* (2006.01)
*A61F 2/08* (2006.01)
*A61B 90/92* (2016.01)

(52) U.S. Cl.
CPC .... *A61B 17/06166* (2013.01); *A61B 17/0401* (2013.01); *A61B 90/92* (2016.02); *A61B 2017/00725* (2013.01); *A61B 2017/00893* (2013.01); *A61B 2017/044* (2013.01); *A61B 2017/0406* (2013.01); *A61B 2017/0417* (2013.01); *A61B 2017/0475* (2013.01); *A61B 2017/0477* (2013.01); *A61B 2017/06176* (2013.01); *A61F 2002/0852* (2013.01); *A61F 2002/0882* (2013.01)

(58) Field of Classification Search
CPC ... A61L 17/00; A61B 17/06; A61B 17/06166; A61B 2017/06176; A61B 2017/0475
See application file for complete search history.

(56) References Cited

U.S. PATENT DOCUMENTS 5,152,790 A * 10/1992 Rosenberg ............ A61F 2/0811
606/304
8,795,334 B2 8/2014 Astorino et al.
2013/0023928 A1* 1/2013 Dreyfuss ............ A61B 17/0401
606/228

OTHER PUBLICATIONS

Perriello, Mike, et al., Displacement of a Fixed Versus Adjustable Suspensory Fixation Device for Anterior Cruciate Ligament Reconstruction, Smith & Nephew, Inc., Jul. 2012, vol. 3, No. 7, 3 pages.
ACL TightRope and EndoButton Biomechanical Testing, Arthrex, Inc. 2013, 1 page.
Ketchum, Suture Materials and Suture Techniques Used in Tendon Repair, Symposium on Flexor Tendon Surgery, Hand Clinics, vol. 1, No. 1, pp. 43-54, Feb. 1985.

(Continued)

*Primary Examiner* — Victor Nguyen
(74) *Attorney, Agent, or Firm* — Kim IP Law Group PLLC

(57) ABSTRACT

A suture fixation device and method thereof is provided. The suture fixation device includes a suture fiber having a length of about 24 to 40 inches and a plurality of knots spaced apart from each other along the length of the suture fiber. Each of the plurality of knots has an overall width of about 3.0 to 4.0 mm.

17 Claims, 18 Drawing Sheets

(56) References Cited

OTHER PUBLICATIONS

Arthrex ACL TightRope and Biomed ZipLoop with ToggleLoc: Mechanical Testing, Arthrex Inc., 2010.
ACL TightRope RT Pin, Fixation, Smooth, Arthrex Inc., Mar. 14, 2012.
Nag et al., Seating of TightRope RT Button Under Direct Arthroscopic Visualization in Anterior Cruciate Ligament Reconstruction to Prevent Potential Complications, Arthrosc. Tech., Sep. 2012; 1(1): e83-e85, New Delhi, India.
Barrow et al., Femoral Suspension Devices for Anterior Cruciate Ligament Reconstruction, The American Journal of Sports Medicine, vol. 42, No. 2, 2014, 343-349.
Watson, Endobutton CL Ultra fixed-length cortical suspension device vs. adjustable-loop fixation designs: Review of Mechanical data, Bone & Joint Science, vol. 04, No. 4, Oct. 2014, pp. 1-9.
Petre et al., Femoral Cortical Suspension Devices for Soft Tissue Anterior Cruciate Ligament Reconstruction: A Comparative Biomechanical Study, The American Journal of Sports Medicine, vol. 41, No. 2, 2012, pp. 416-422.
Q-Fix brochure, ArthroCare Corporation, Jan. 2015.
Q-fix Technique guide, ArthroCare Corporation, Jan. 2015.
Brouwers et al., Dynamic Loading of Surgical Knots, Surgery, Gynecology & Obstetrics, Dec. 1991, vol. 173, pp. 443-448.
Nilsson, Effect of Strain Rate on Tensile Strength and Strain of Surgical Suture Materials, Scandinavian Journal of Plastic and Reconstructive Surgery, 1982, vol. 16, No. 2, pp. 97-100.
Nilsson, Mechanical Properties of Prolene® and Ethilon® Sutures After Three Weeks in Vivo, Scandinavian Journal of Plastic and Reconstructive Surgery, 1982, vol. 16, No. 1, pp. 11-15.
ACL TightRope Screenlife Update Arthrex Inc., 2016.

\* cited by examiner

SUTURE FIXATION DEVICE AND METHOD THEREOF

CROSS-REFERENCE TO RELATED APPLICATIONS

This application claims the benefit of U.S. Provisional Application No. 62/204,027, filed Aug. 12, 2015, the entire disclosure of which is incorporated by reference herein in its entirety.

BACKGROUND OF THE INVENTION

The present invention relates generally to a suture fixation device and method thereof for attaching e.g., a graft, to bone. In particular, the present invention relates to a suture fixation device having a plurality of knots for securing.

During anterior cruciate ligament (ACL) reconstruction, the old ligament is removed and bone tunnels are made to place the new ligament (patellar graft) or tendons in the knee at the site of the old ACL. Conventional fixation devices, such as suture screws, anchors, buttons, and pins, are typically used in many orthopedic repair procedures, including: ACL fixation, ACL joint reconstruction, and bone fracture fixation. While these devices are commonly used to perform these procedures, they are cost ineffective. Each device can cost hundreds of dollars which is a financial burden to hospitals, surgeons, patients and insurers. Thus, there is still a need for a more efficient and economical fixation device for fixation in orthopedic repair procedures.

BRIEF SUMMARY OF THE INVENTION

In accordance with an exemplary embodiment, the present invention provides suture fixation device comprising: a suture fiber having: a length of about 24 to 40 inches; and a plurality of knots spaced apart from each other along the length of the suture fiber, wherein each of the plurality of knots have an overall width of about 3.0 to 4.0 mm. The suture fixation device further includes growth factors infused within suture fiber.

In accordance with another exemplary embodiment one of the plurality of knots is a sliding knot. The suture fixation device further includes pouch wings to secure the sliding knot to another of the plurality of knots.

In accordance with yet another exemplary embodiment, the present invention provides a method of securing tissue to bone comprising using a suture fixation device comprising a plurality of knots, forming a through hole in a bone, passing a first end of the suture fixation device through the through hole, securing the first end of the suture fixation device to tissue, and forming a securing knot about a second end of the suture fixation device at a position along the length of the suture fiber such that tension is applied to the tissue.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Reference will now be made in detail to the preferred embodiments of the invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. Such directional terms used in conjunction with the following description of the drawings should not be construed to limit the scope of the invention in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges throughout this disclosure and various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the embodiments of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Figure 26:
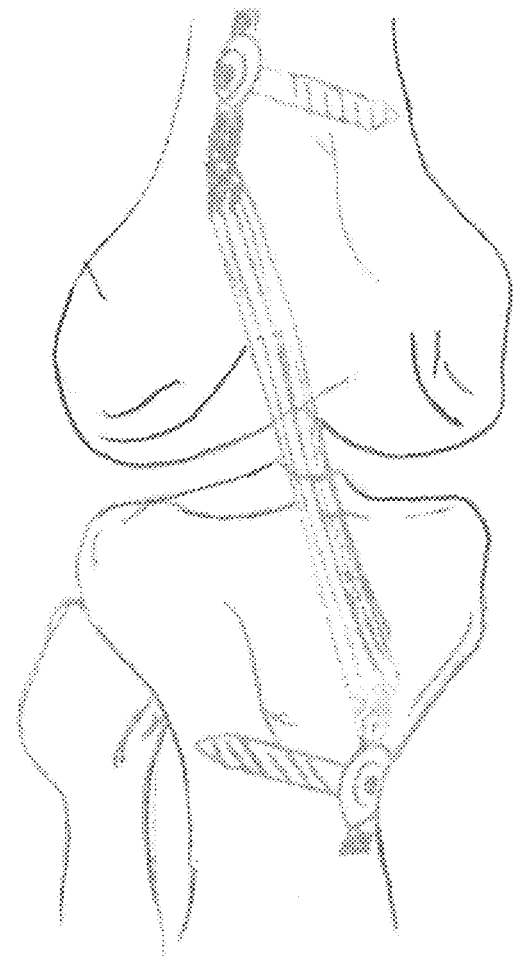
FIG. 26 is an anterior view of a graft attached to a tibia and femur of a knee joint with bone screws.

FIG. 26 illustrates a standard method of affixing graft to bone via screws, anchors, or pins.

In accordance with an exemplary embodiment of the present invention, there is provided a suture fixation device 10, as shown in FIGS. 27-29C. The suture fixation device comprises a plurality of suture fibers or sutures. Sutures applicable to the present invention are disclosed e.g., in U.S. Pat. No. 8,795,334, the entire disclosure of which is incorporated by reference herein in its entirety for all purposes. The suture fixation device is a single use suture fiber fixation device that can be used to replace conventional suture screws, buttons, pins, and anchors used for tendon to bone reconstruction. The suture fixation device is directed to suture fixation for orthopedic reconstruction using effective knots with surgical fiber sutures. In general, sutures are indicated for use in general soft tissue approximation and/or ligation. The present exemplary embodiments of the suture fixation device includes a method and suture materials to provide an enhanced fixation means while being more cost effective.

The present invention provides a method and apparatus for graft fixation in orthopedic reconstruction procedures by incorporating knots to a suture fiber that will affix ligament or tendon to bone. The suture fixation device being comprised of suture fibers is invisible within X-ray wavelengths to prevent any image distortion. If, metal screws and plates are used in combination with the suture fixation device, or needed during additional or other orthopedic procedures, the suture fiber will not interfere with the procedure since it is only used to apply tension and pressure for fixation.

The suture fixation device is composed of a single or double suture fiber with several knots pre-tied along the fiber. For example, during an ACL reconstruction, a surgeon replaces the torn ACL ligament using several choices of tissue to use for the new ligament, including an autograft (tissue from the patient's own body) or an allograft (tissue from a cadaver). One of the most common autografts use part of the patellar tendon (the tendon in the front of the knee). The old ligament is removed using a shaver or other instruments.

Bone tunnels or through holes are made to place the new ligament (patellar graft) in the knee at the site of the old ACL. Instead of screws to secure the graft in the bone tunnels, the suture fixation device is inserted using an eyelet and deployed with an arthroscopic instrument (e.g., knot pusher). Once the last knot passes through bone tunnel, the surgeon pulls on the suture to create one larger securing knot. The securing knot will be strong enough to affix the tendon in place until tissue cells grow over during the healing process. The suture fixation device is to be used in two entry points—in the femur and in the tibia.

In accordance with an exemplary embodiment of the present invention, the suture fixation device 10 includes a plurality of knots 12 e.g., 2, 3, 4, 5, 6, 7, 8 or more knots. Each knot has a defined or predetermined size e.g., 2, 2.5, 3, 3.5, 4, 4.5, 5, 5.5, 6, 6.5, 7 mm or more. The predetermined size of the know 12 can be varied depending on the size of a patient or patient's bone.

In accordance with another exemplary embodiment, the suture fixation device 10 is configured to have an overall from about 24 to 40 inches, but can be more or less depending on the size of a patient or patient's bone. For example, the length of the fibers of the suture can range from about 22, 24, 26, 28, 30, 32, 34, 36, 38, 40 and 42 inches.

In accordance with yet another exemplary embodiment, the suture fixation device 10 is color coded. That is, the suture fixation device is provided with different color fibers. For example, a first colored end of the suture fixation device is used to anchor the suture fiber onto graft and a second colored end of the suture fixation device is used to pull the suture fiber to create one large knot or bone containing knot or a securing knot 14. The second color differs from the first color.

In accordance with another exemplary embodiment, the suture fixation device is formed from non-absorbable suture fibers or absorbable suture fibers. The suture fixation device can be infused with growth factors.

Figure 12:
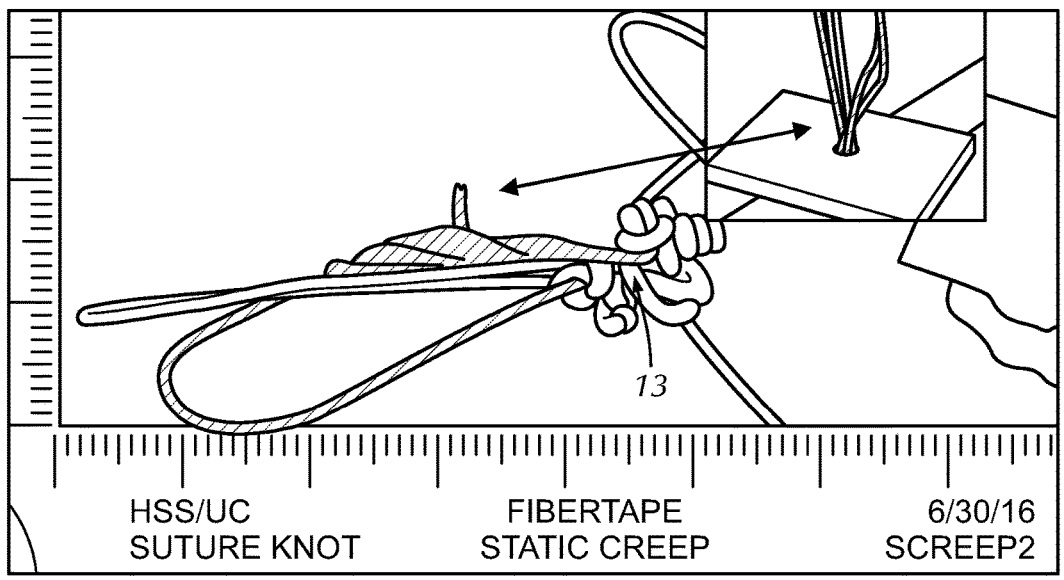
Figure 13:
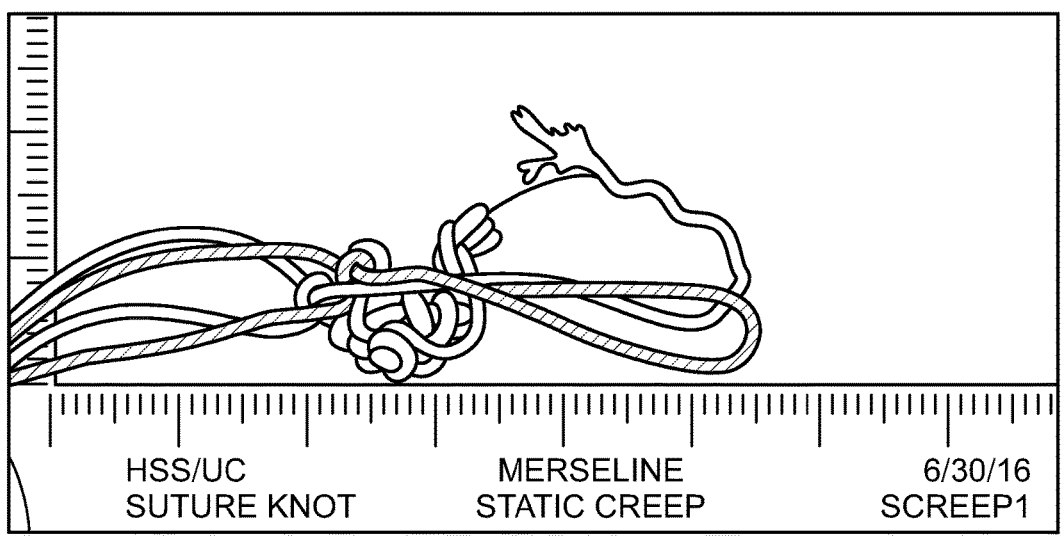
Figure 14:
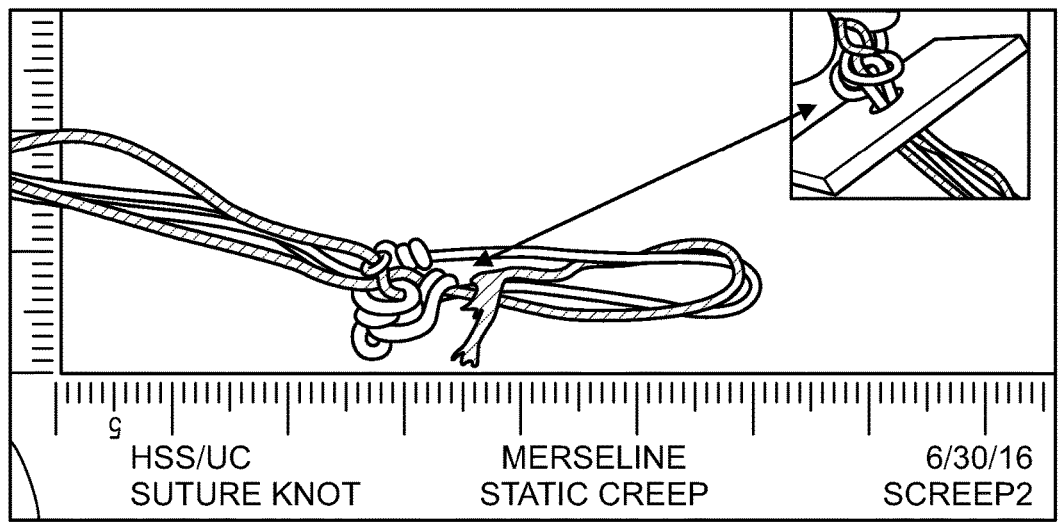
Figure 15:
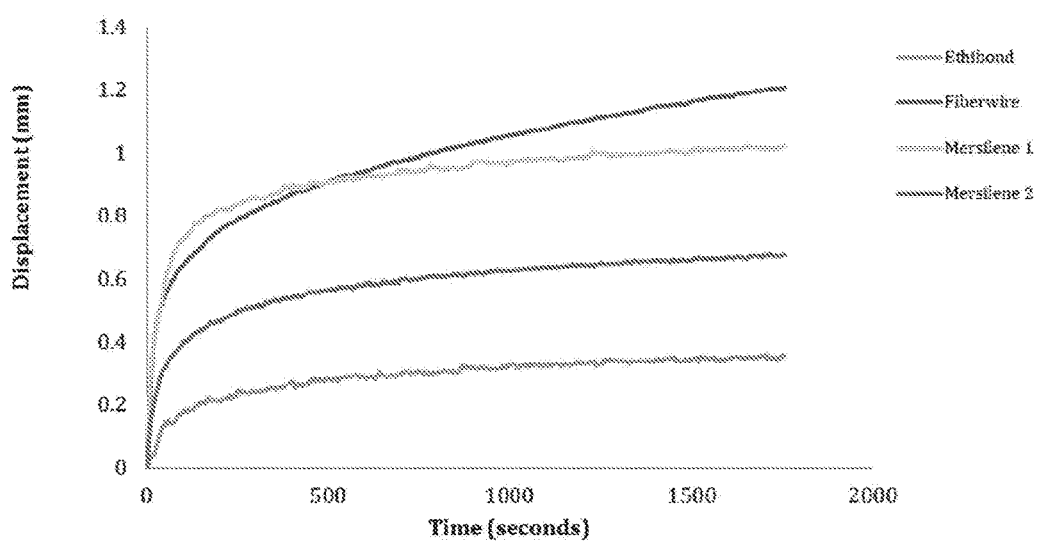
FIG. 15 is a graph of displacement versus time for the evaluation of the exemplary suture fixation devices of FIGS. 1-3.
Figure 16:
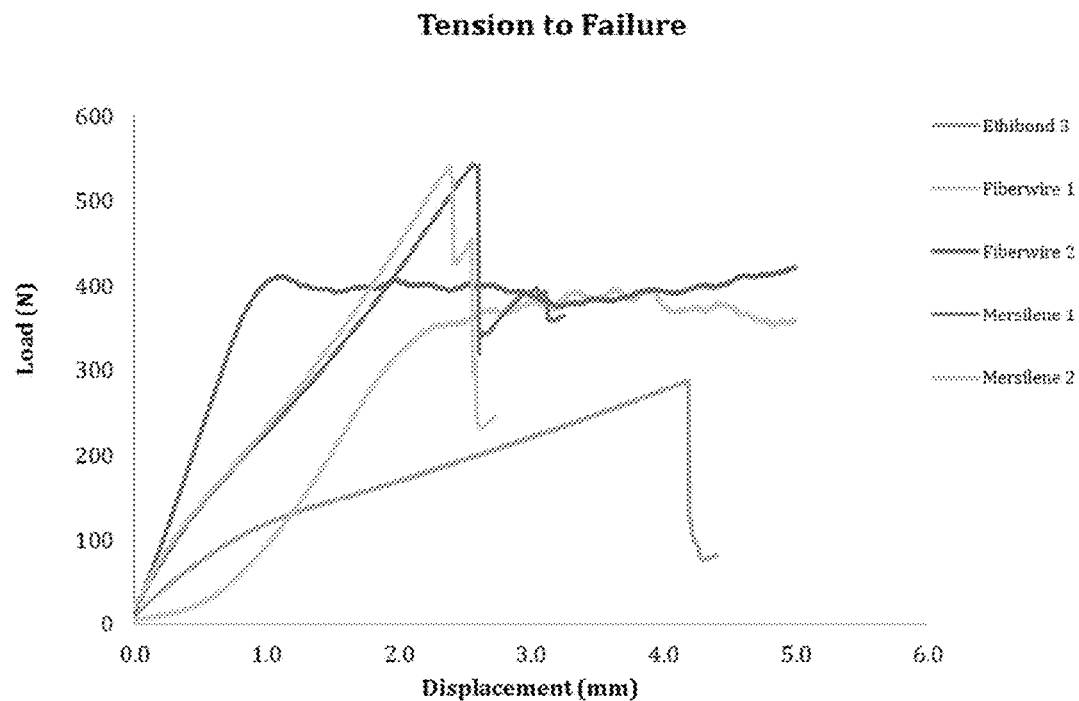
FIG. 16 is a graph of load versus displacement for the evaluation of the exemplary suture fixation devices of FIGS. 1-3.
Figure 17:
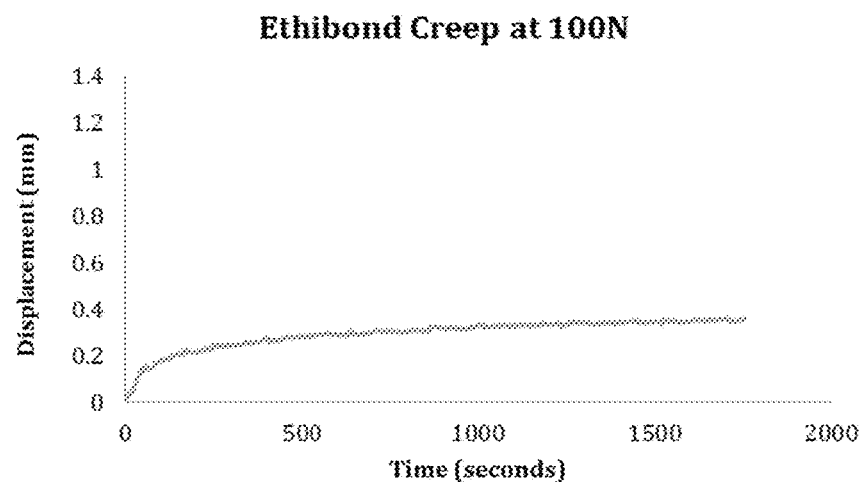
FIGS. 17-25 are graphs of the evaluation results of the evaluation of the exemplary suture fixation devices of FIGS. 1-3.
Figure 18:
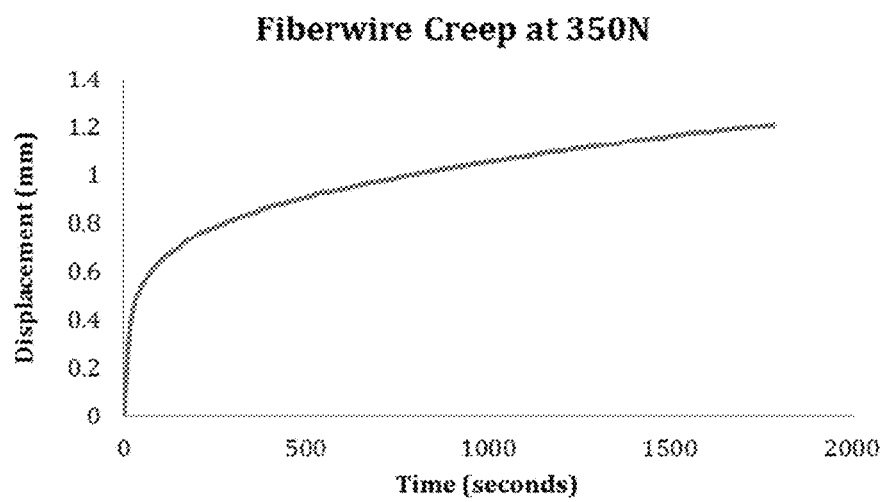
Figure 19:
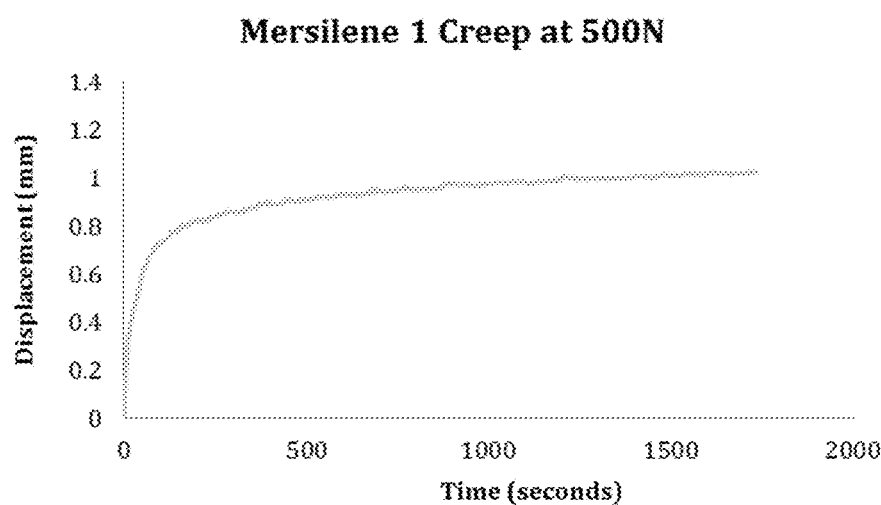
Figure 20:
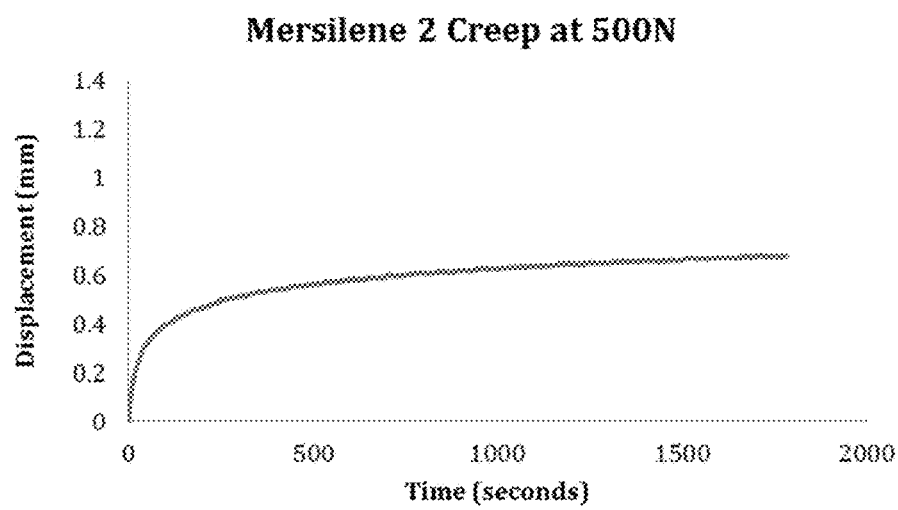
Figure 21:
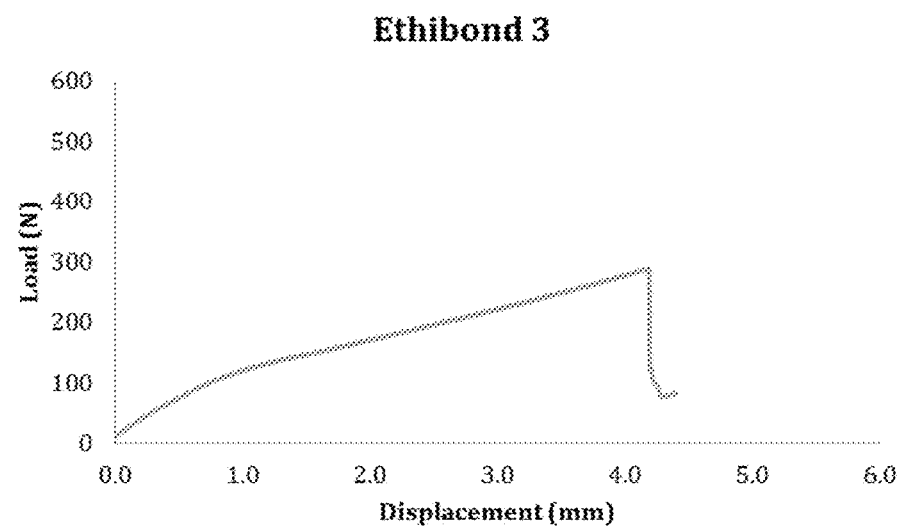
Figure 22:
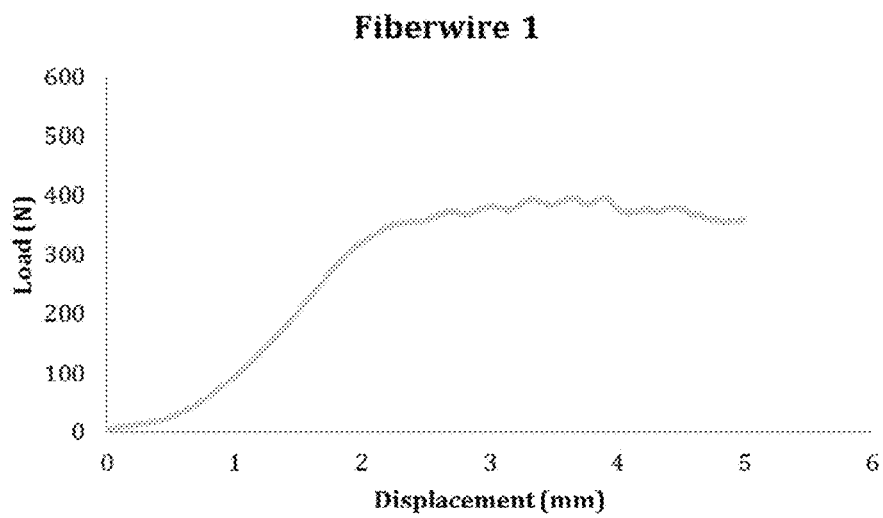
Figure 23:
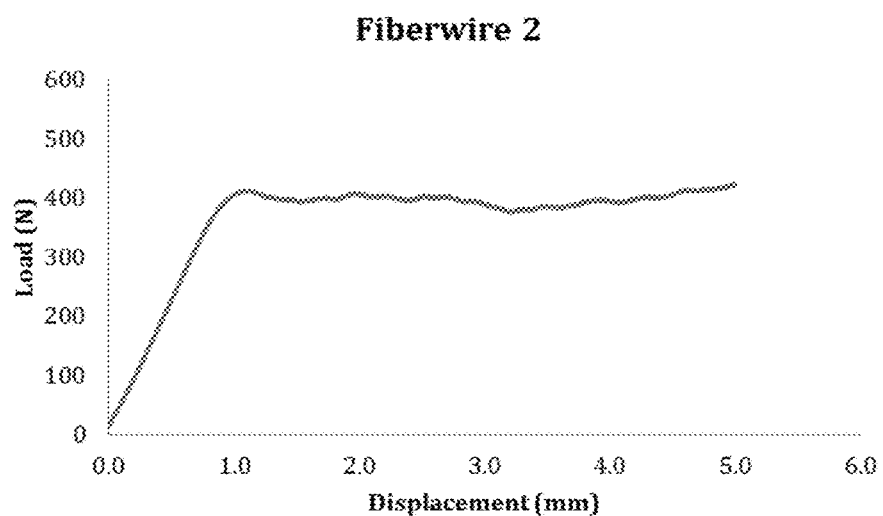
Figure 24:
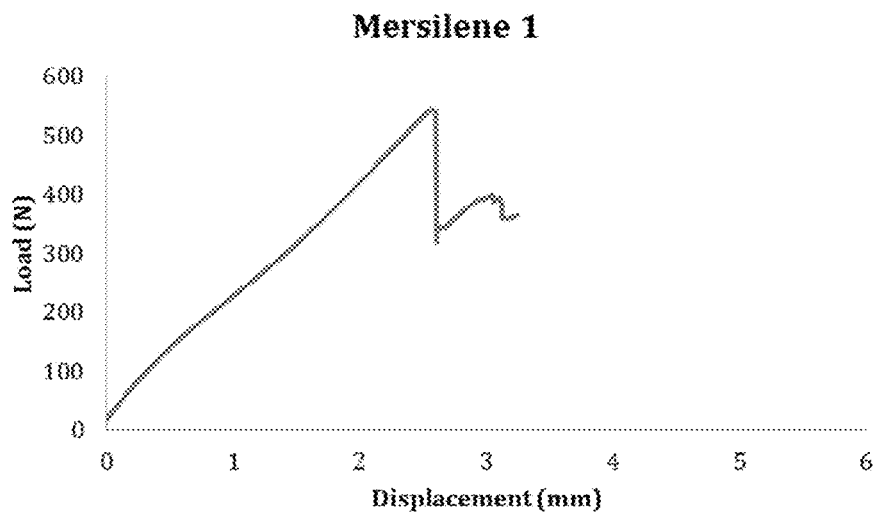
Figure 25:
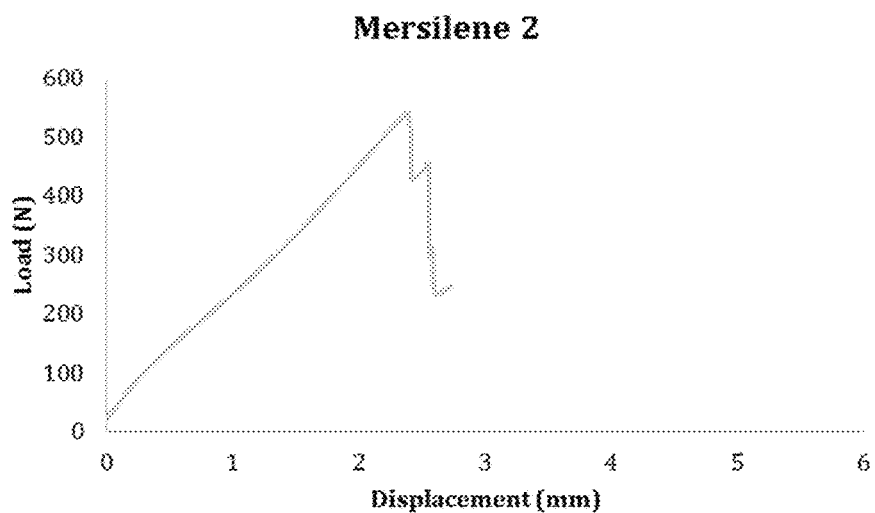

In accordance with yet another exemplary embodiment, the plurality of knots 12 has at least one of its knots formed as a sliding knot 12b. The sliding knot to secure the other of the plurality of knots with pouch wings 13 (FIG. 12) for platelet rich plasma or stem cells.

In operation, the plurality of knots 12 of the suture fixation device is used e.g., for tendon to bone reconstruction.

Figure 27:
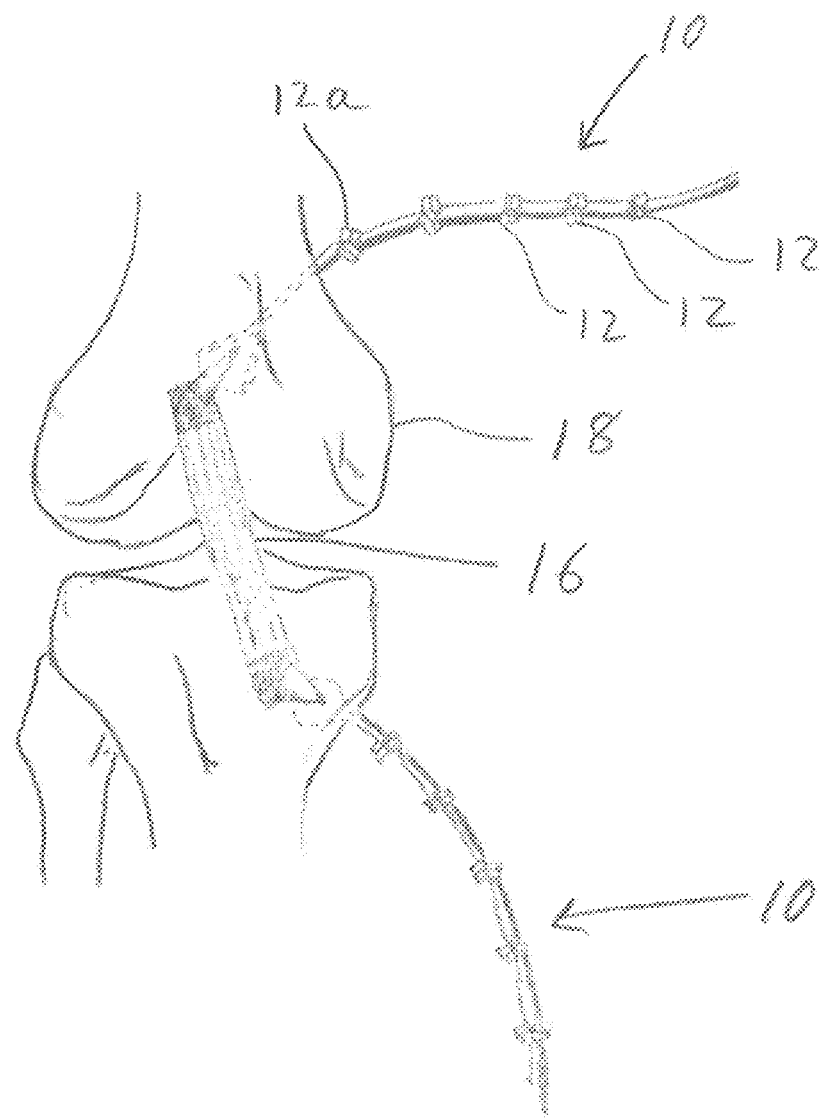
FIG. 27 is an anterior view of a grant and suture fixation device in accordance with an exemplary embodiment of the present invention assembled to a knee joint.
Figure 28:
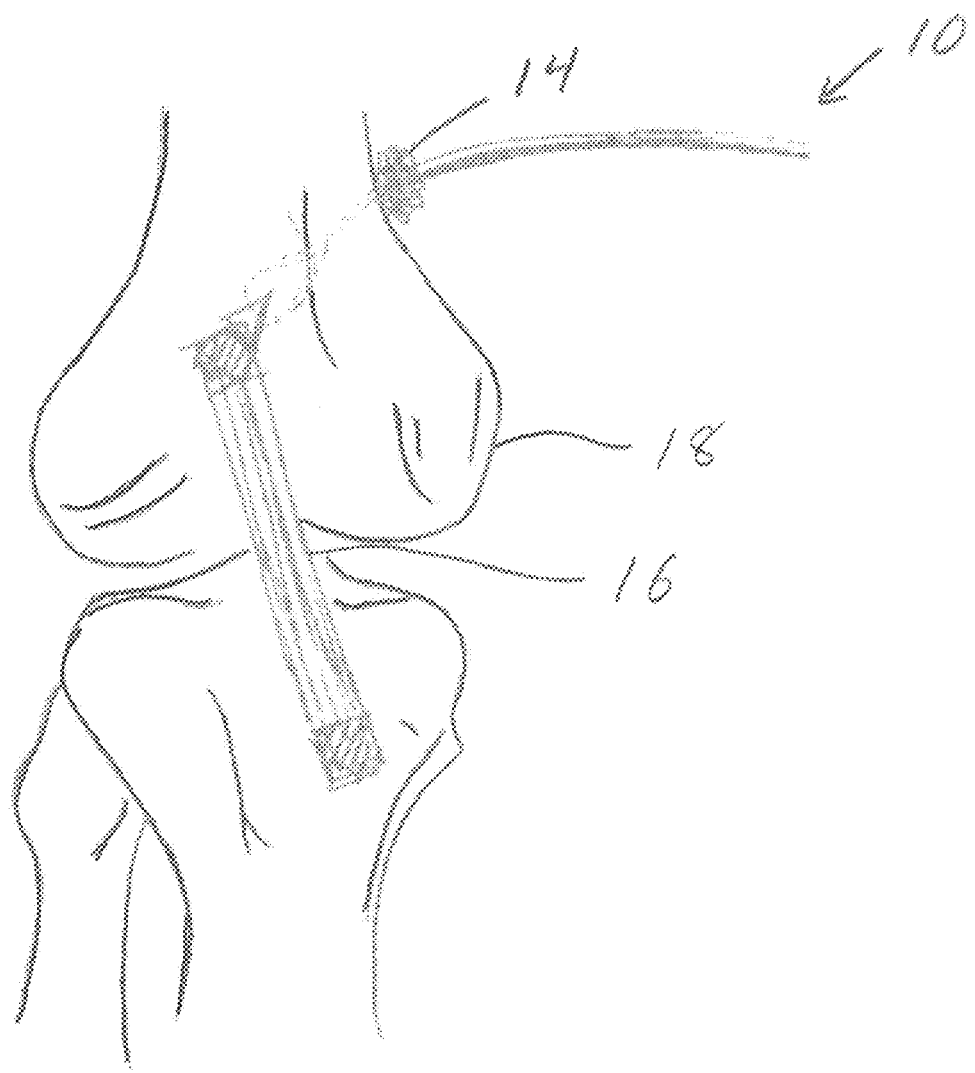
FIG. 28 is an anterior view of the knee joint of FIG. 27 with the suture fixation device formed into a securing knot.

In accordance with an exemplary method of the present invention, sutures instead of screws or other metal fasteners are used e.g., for ACL repair, as shown in FIGS. 27 and 28. FIG. 27 illustrates placement of the suture fixation device 10 having a plurality of knots 12 on a tibia and femur of a knee joint. FIG. 28 illustrates the securing knot 14 formed when it is affixed along the cortex of the bone for securing the graft 16 to the femur 18.

Figures 29A, 29B, 29C:
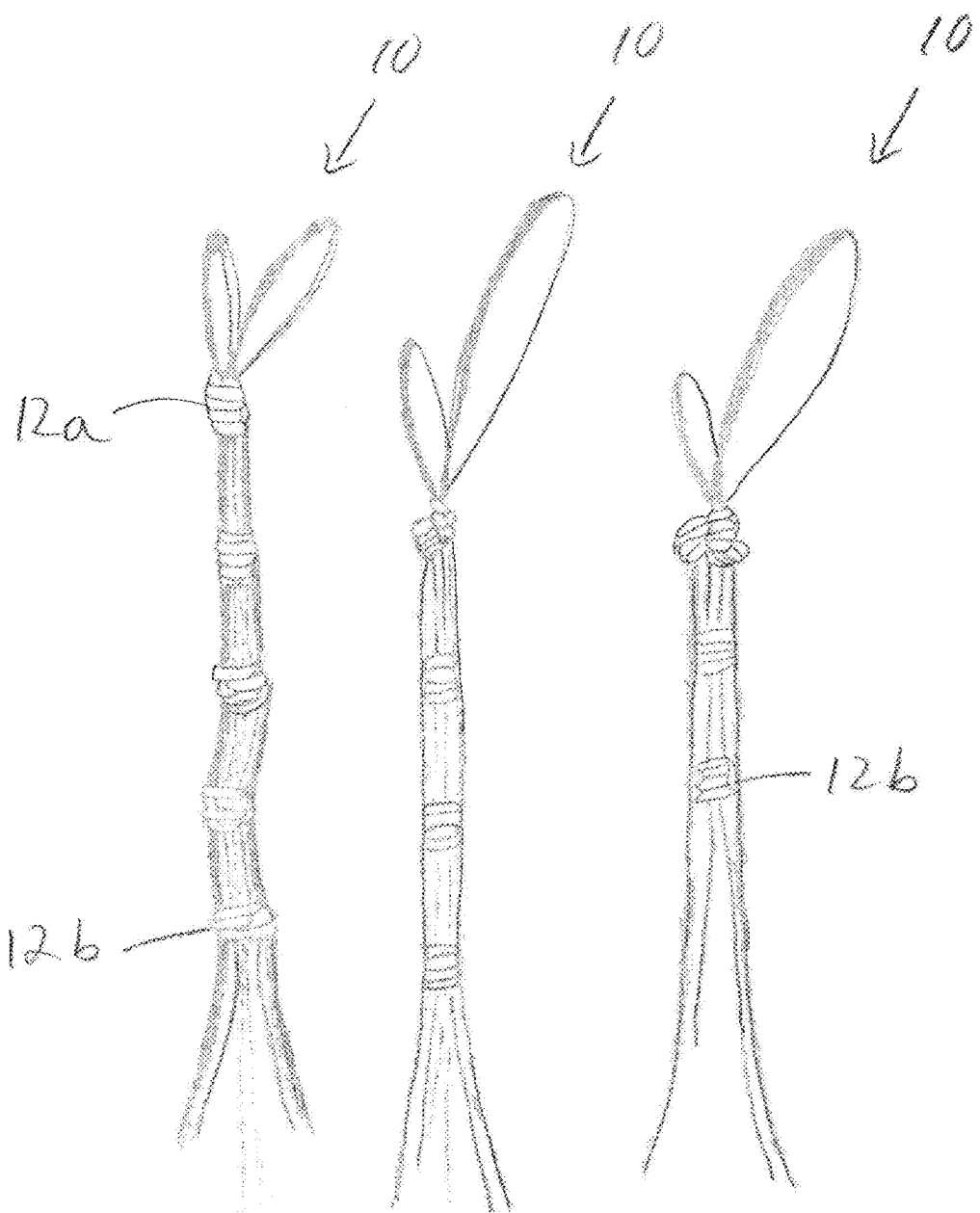
FIGS. 29A-29C are a series of figures illustrating a method of forming a securing knot in accordance with an exemplary embodiment of the present invention.
Figure 30A:
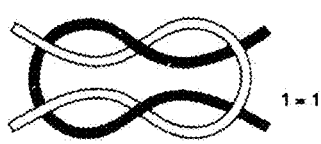
FIGS. 30A-G show knots applicable to the suture fixation device in accordance with the present invention.
Figure 30B:
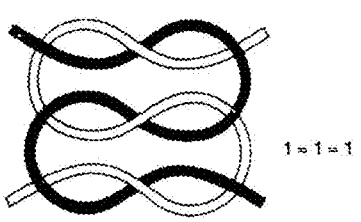
Figure 30C:
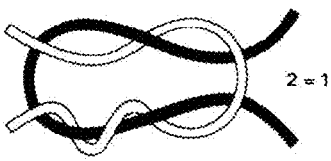
Figure 30D:
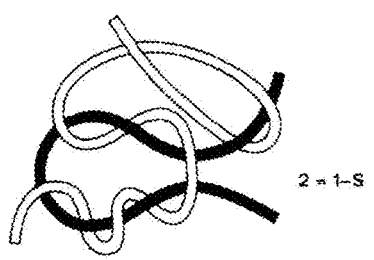
Figure 30E:
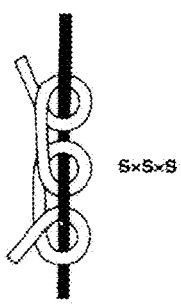
Figure 30F:
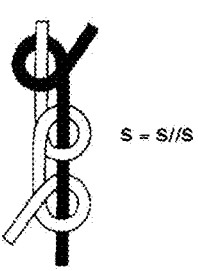
Figure 30G:
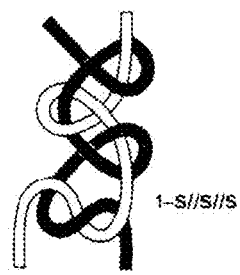

FIGS. 29A-C illustrate an exemplary method in which the securing knot 14 is formed. Specifically, the securing knot 14 is formed by pulling on one suture and the plurality of knots will gather to a first knot position 12a along the loop of the suture fixation device.

The method can be used to affix tendon, ligament or other tissue to bone using the suture fixation device.

One end of the suture fixation device is attached to e.g., graft 16, at multiple points so as to be able to apply tension on the graft over a relative large area in order to avoid bone collapse failure. The suture fixation device can alternatively be attached to the graft using e.g., a reamer.

In accordance with another exemplary method, the present invention provides for using the suture fixation device 10, forming a through hole in a bone, passing a first end of the suture fixation device through the through hole, securing the first end of the suture fixation device to tissue, and forming a securing knot about a second end of the suture fixation device at a position along the length of the suture fiber such that tension is applied to the tissue. The through hole can be e.g., about 1, 2, 3, 4, 5, 6 mm or more in diameter, but alternatively can be more or less.

Knots applicable to the exemplary embodiments of the present invention are shown in FIG. 30 and include e.g., square—1=1, 2=1, 2=1–S and 1=1=1—and sliding—S×S× S, S=S//S and 1–S//S//S. Suture materials applicable to the exemplary embodiments of the present invention include, but are not limited to, plain catgut, Dexon [polyglycolic acid], Maxon [polyglyconate], PDS [polydiaxone], Prolene [polypropylene].

Suture techniques for securing the suture fixation device to tissue or other materials include interrupted sutures, Bunnell, Nicoladoni technique, Mason-Allen stitch, lateral trap technique, Kessler grasphing suture, end-weave anastomosis, and fish-mouth anastomosis of Pulvertaft.

Evaluations of various exemplary suture fixation devices (SFD) will now be discussed.

Experimental Evaluation

Sample Description

Figure 1:
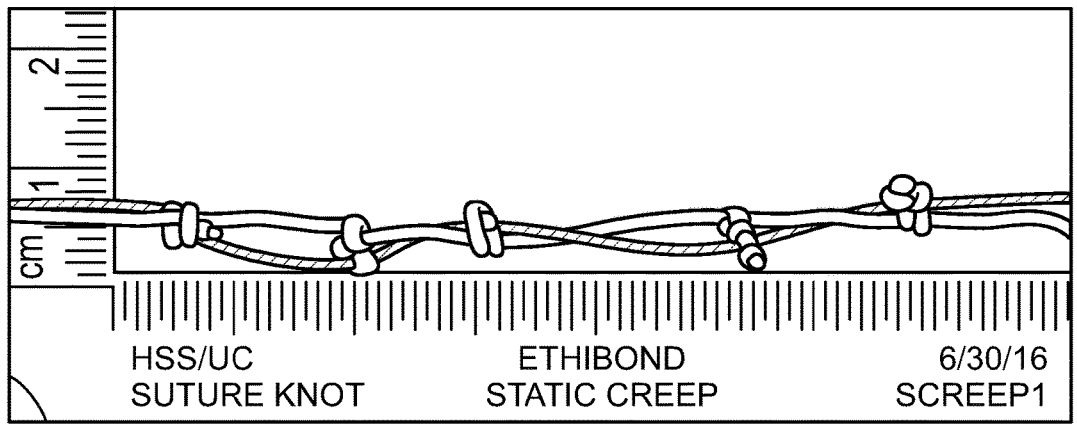
FIGS. 1-3 illustrate exemplary suture fixation devices in accordance with the present invention used in an evaluation.
Figure 2:
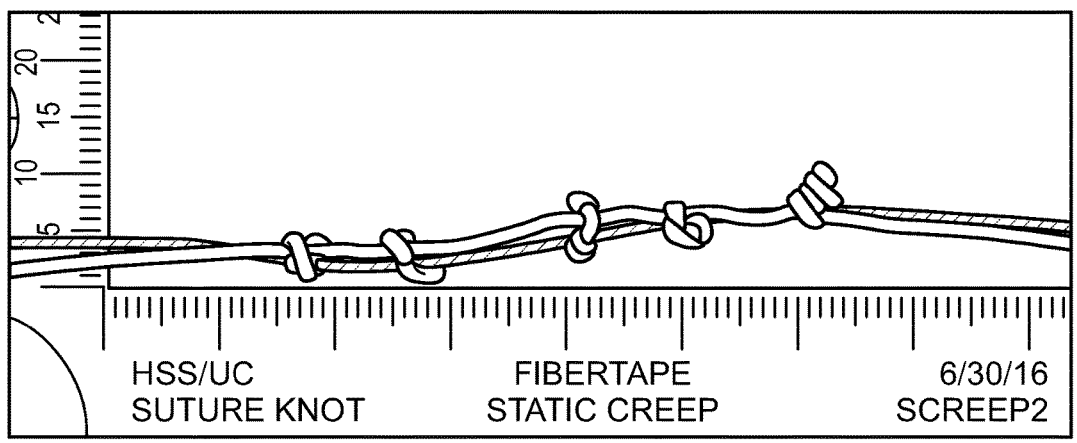
Figure 3:
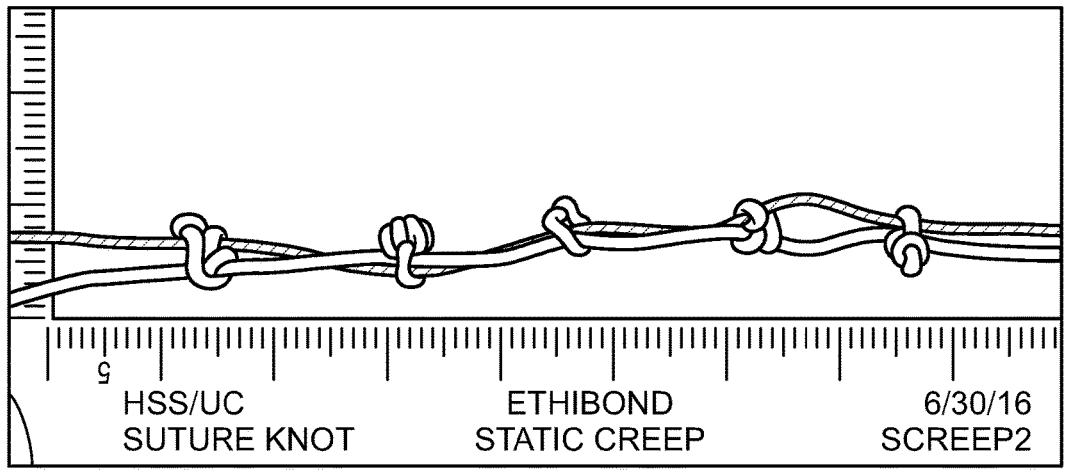

Three (3) SFDs were provided by the study sponsor and were assessed using the methods outlined in Table 1. The SFD was comprised of two lengths of suture. The first 'knotted' length consisted of five (5) knots spaced approximately 10 mm apart at the center of the suture length. The second 'threaded' suture was aligned parallel with the knotted suture and threaded through the five knots. FIGS. 1 through 3 show representative photographs of the SFDs.

TABLE 1

TEST PLAN

| SUTURE | CONSTRUCT DESCRIPTION | TEST METHOD | QTY |
| --- | --- | --- | --- |
| Ethibond | Knotted Number 5 Ethibond Suture threaded with Number 2 Ethibond Suture | 30 mins Creep at 100N - Tension to Failure | 3 |
| Fiberwire | Knotted Number 5 Fiberwire Suture threaded with Number 2 Fiberwire Suture | 30 mins Creep at 350N - Tension to Failure | 2 |
| Mersilene | Knotted Number 6 Mersilene Suture threaded with Number 6 Mersilene Suture | 30 mins Creep at 500N - Tension to Failure | 2 |

Materials

Figure 4:
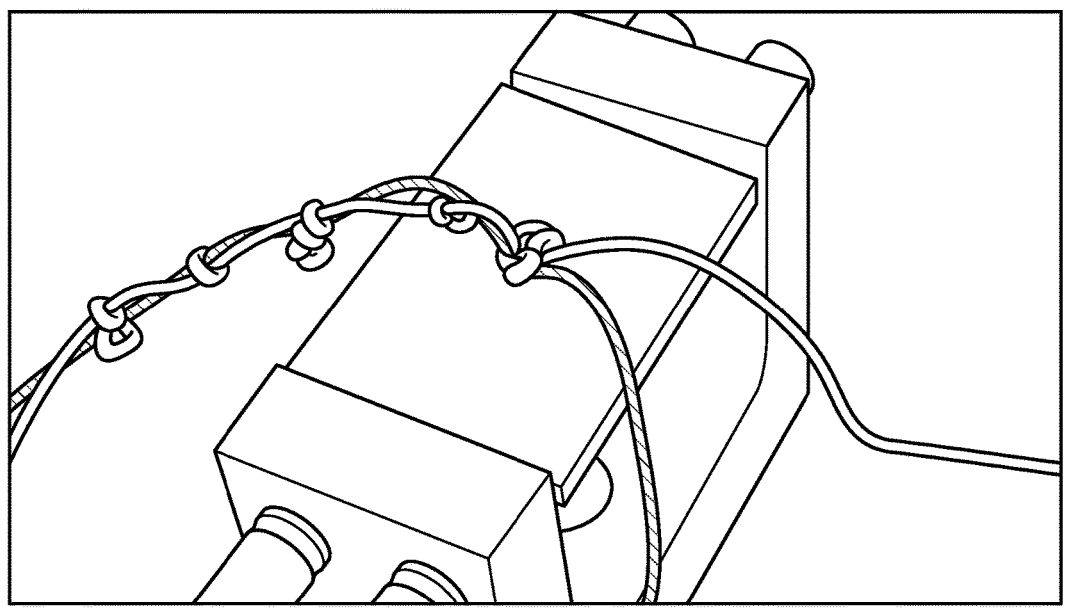
FIGS. 4-7 illustrate testing apparatus used in the evaluation of the exemplary suture fixture devices of FIGS. 1-3.
Figure 5A:
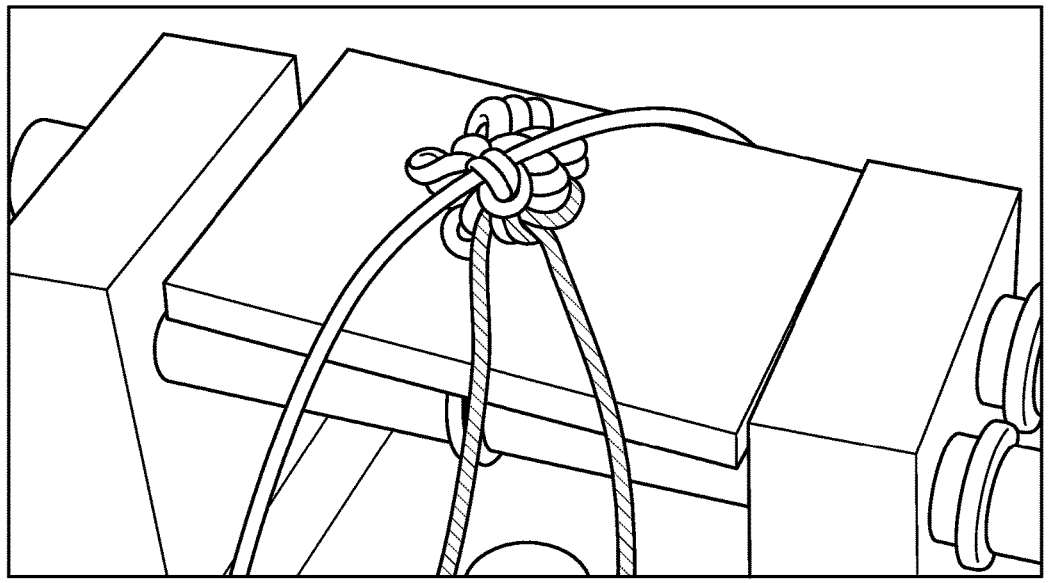
Figure 5B:
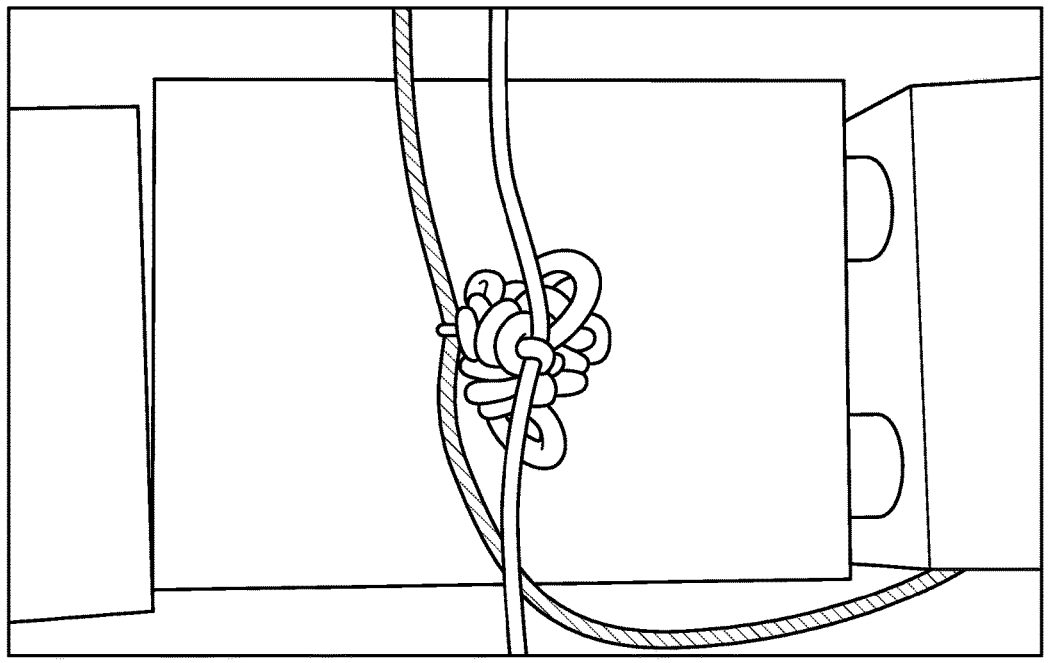

The following materials and equipment were utilized to complete the testing.
(1) Servo-Hydraulic Testing Machine.
(3) Ethibond Suture Knot Constructs with:
  knotted Number 5 Ethibond Excel Suture cord, PN: D6296, LN: None
  threaded Number 2 Ethibond Excel Suture cord, PN: MX69, LN: None
(2) Fiberwire Suture Knot Constructs with:
  knotted Number 5 Fiberwire Suture cord, PN: AR-7210, LN: 13490
  threaded Number 2 Fiberwire Suture cord, PN: AR-7200, LN: 12964
(2) Mersilene Suture Knot Constructs with:
  knotted Number 6 Mersilene Suture cord, PN: D2135, LN: None
  threaded Number 6 Mersilene Suture cord, PN: D2135, LN: None
(1) Stainless Steel Test Fixture Set
(1) 5 mm thick Aluminum Plate with centered Ø3 mm Hole
(- -) Assorted Hand Tools Methods Setup SFD constructs were assembled. Briefly, both distal ends of the SFD (knotted and threaded) were threaded through a Ø3 mm hole in an aluminum plate, fed around two parallel stainless steel rods and then back through the hole in the aluminum plate creating a loop. The hole had been dressed on the top and bottom of the plate until the edges were smooth. Both ends of the distal suture cords i.e., SFD, were pulled until the first knot in the construct was engaged at the top of the Ø3 mm hole. The proximal end of the knotted suture cord was pulled tight and held with tension maintained. The proximal end of the threaded suture cord was pulled tight, thereby pulling the five (5) knots in the knotted suture cord together into a tight mass against the top of the Ø3 mm hole. Both ends of the threaded suture cord were then secured on the knotted mass using a square knot. Both ends of the knotted suture were pulled tight around the knotted mass and secured using a square knot. FIGS. 4 and 5 show representative photographs of the construct setup.

Creep

Constructs were mounted to the testing machine by suspending the suture loop created during construct setup over a stainless steel hook secured to the actuator of the servo hydraulic testing machine. The aluminum plate was constrained to the base of the testing machine underneath two (2) parallel stainless steel rods, with the suture loop passing between the rods. A 10 N tensile preload was applied to the construct for 30 seconds and displacement was tared.

Each construct was subjected to 10 preconditioning cycles at 0.5 Hz at the loads levels outlined in Table 2. Following preconditioning, tensile load was applied to each specimen at a rate of 5 N/second under load control until the prescribed creep load was achieved. This load was then maintained for 30 minutes with the testing machine operating in load control. Load and displacement data were recorded for the duration of the creep at a rate of 10 Hz. The change in displacement observed over the 30 minutes of creep was determined for each specimen.

Figure 6:
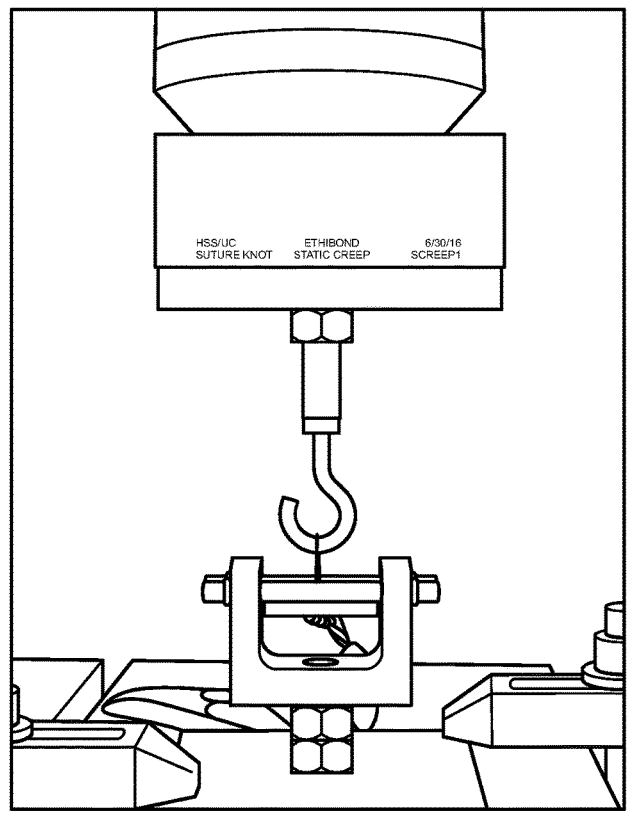
Figure 7:
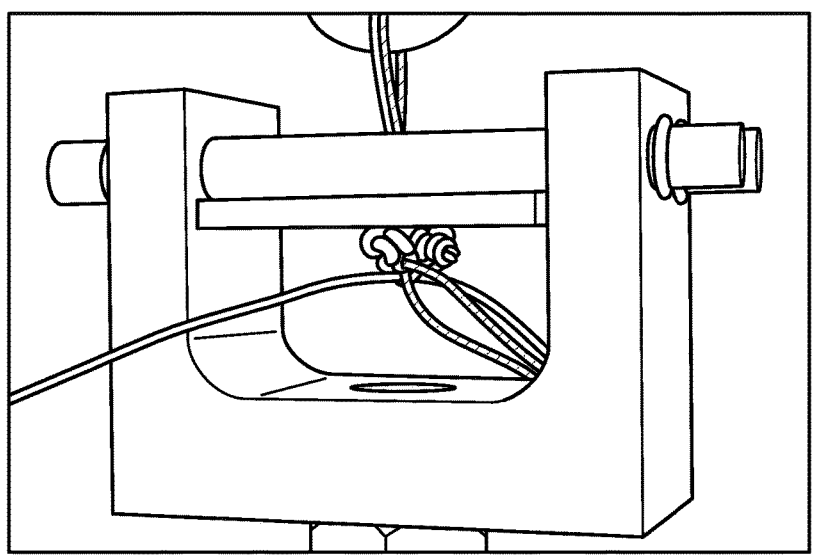
Figure 8:
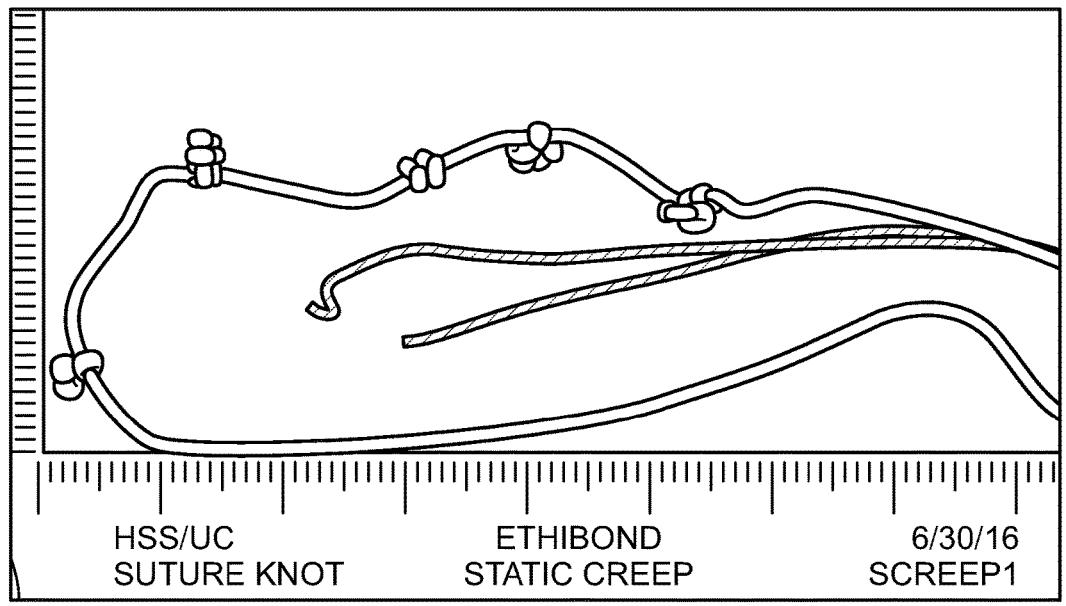
FIGS. 8-14 illustrate the exemplary suture fixation devices of FIGS. 1-3 after evaluations.
Figure 9:
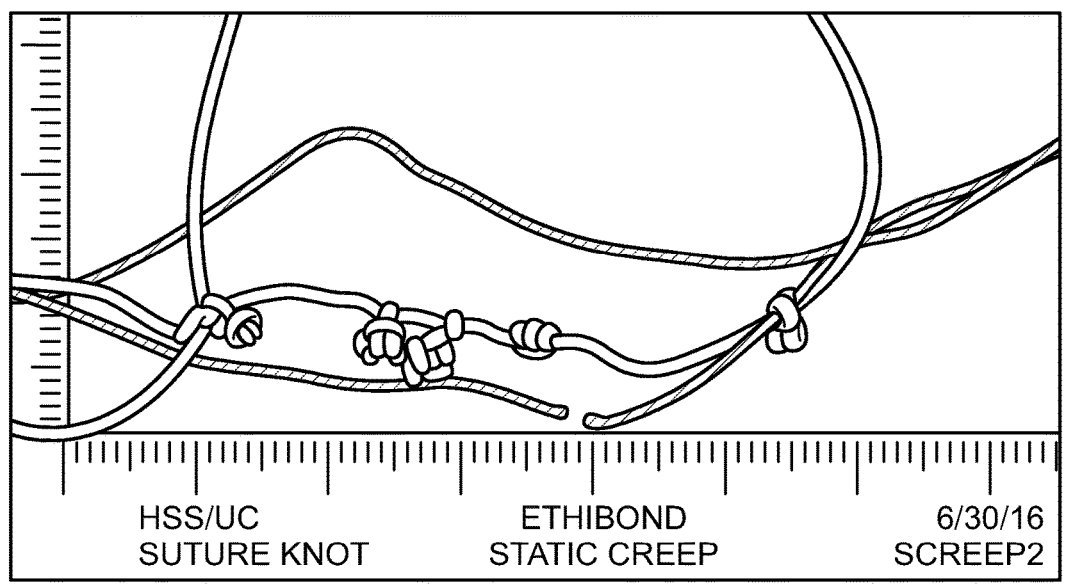
Figure 10:
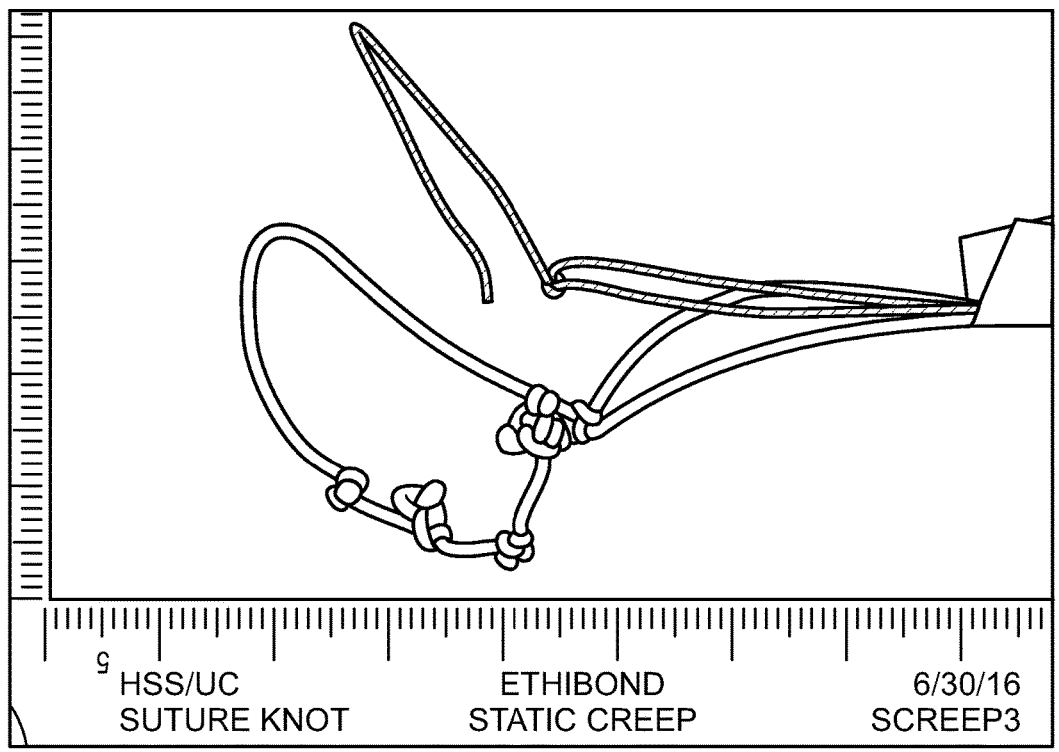
Figure 11:
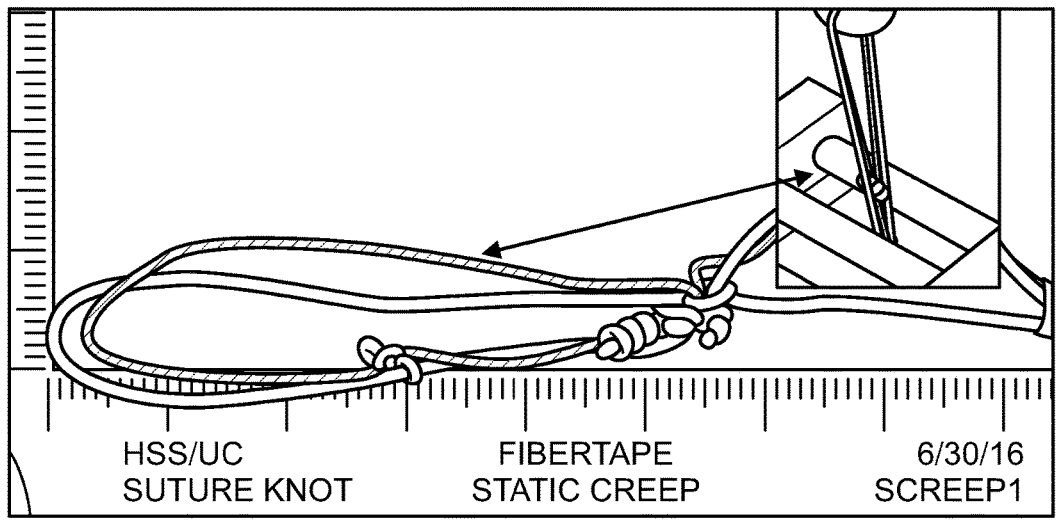

FIGS. 6 and 7 show representative photographs of the construct configuration for creep testing. The static results for each test are tabulated and shown in FIGS. 17-25.

TABLE 2

CREEP TEST PLAN

| SUTURE | CONSTRUCT | PRECONDITIONING (10 cycles) | CREEP (30 minutes) |
| --- | --- | --- | --- |
| Ethibond | 1 | 20-200N | —[1] |
| | 2 | 15-150N | —[1] |
| | 3 | 7.5-75N | 100N |
| Fiberwire | 1 | —[2] | —[2] |
| | 2 | 10-100N | 350N |
| Mersilene | 1 | 10-100N | 500N |
| | 2 | 10-100N | 500N |

[1]Construct failed during preconditioning
[2]Construct was not tested in creep

Tension to Failure

Constructs were unloaded and displacement was zeroed following the creep tests. A tensile load was applied to the suture loop at 5 mm/minute in displacement control until failure occurred. Failure was designated as a rapid loss in tensile force and/or rupture of the suture material.

Load and displacement data were recorded for the duration of the test at a rate of 100 Hz. The mode and location of failure was noted for each sample. Peak load and stiffness were determined for each sample. The static results for each test are tabulated and shown in FIGS. 17-25.

Results

Failure Mechanisms

The failure mechanisms for each construct are shown in Table 3. In the Ethibond and Fiberwire constructs, failure occurred in the knot or loop of smaller diameter 'threaded' suture which secured the knotted suture mass together. In the Mersilene constructs, the first sample failed through the first knot of the knotted suture at the interface with the Ø3 mm hole in the aluminum plate. The second sample failed through the threaded suture loop where it interfaced with the edge of the Ø3 mm hole in the aluminum plate. FIGS. 8 through 14 show photographs of each construct at failure.

TABLE 3

FAILURE MECHANISMS

| SPECIMEN | FAILURE MECHANISM |
|---|---|
| Ethibond 1 | Failure at the square knot in the threaded suture securing the knotted suture mass together |
| Ethibond 2 | Failure of the threaded suture in the loop securing the knotted suture mass together |
| Ethibond 3 | Failure of the threaded suture in the loop securing the knotted suture mass together |
| Fiberwire 1 | No defined failure. The first knot pulled though the Ø3 mm hole in the aluminum plate. |
| Fiberwire 2 | Failure through the threaded suture in the loop securing the knotted suture mass together and interface with the Ø3 mm hole in the aluminum plate. |
| Mersilene 1 | Failure through the knotted suture within the first knot entering the Ø3 mm hole in the aluminum plate. |
| Mersilene 2 | Failure through the threaded suture in the loop securing the knotted suture mass together and interface with the Ø3 mm hole in the aluminum plate. |

Creep

The creep results for each suture construct are shown in Table 4. The largest creep of 1.21 mm was measured in the Fiberwire suture construct at 350 N load. The smallest creep of 0.35 mm was measured in the Ethibond suture constructs at 100 N load. Under the highest creep load of 500 N, there was a mean creep of 0.88 mm in the Mersilene suture constructs.

TABLE 4

CREEP RESULTS

| CONSTRUCT | LOAD (N) | DURATION (Minutes) | CREEP DISPLACEMENT (mm) |
|---|---|---|---|
| Ethibond 3 | 100 | 30 | 0.35 |
| Fiberwire 2 | 350 | 30 | 1.21 |
| Mersilene 1 | 500 | 30 | 1.04 |
| Mersilene 2 | 500 | 30 | 0.72 |

Tension to Failure

The tension to failure results for each suture construct are displayed in Tables 5 through 7. The Ethibond had the lowest tension to failure results with a stiffness of 138.8 N/mm and peak load of 198.1±77.8 N. The Fiberwire constructs were the stiffest with a mean stiffness of 331.5±164.5 N/mm and a peak load of 433.3±52.2 N. The Mersilene constructs had the highest peak load of 542.4±1.2 with a stiffness of 269.3±6.2 N/mm.

TABLE 5

ETHIBOND TENSION to FAILURE RESULTS

| SPECIMEN | STIFFNESS [N/mm] | ULTIMATE DISPLACEMENT [mm] | PEAK LOAD [N] |
|---|---|---|---|
| Ethibond 1 | — | — | 156.4[1] |
| Ethibond 2 | — | — | 150.0[1] |
| Ethibond 3 | 138.8 | 4.18 | 287.9 |
| Mean | 138.8 | 4.18 | 198.1 |
| ±SD | — | — | 77.8 |

[1]Construct failed during preconditioning

TABLE 6

FIBERWIRE TENSION to FAILURE RESULTS

| SPECIMEN | STIFFNESS [N/mm] | ULTIMATE DISPLACEMENT [mm] | ULTIMATE LOAD [N] |
|---|---|---|---|
| Fiberwire 1 | 215.2 | 3.62 | 396.4 |
| Fiberwire 2 | 447.8 | 9.26 | 470.2 |
| Mean | 331.5 | 6.44 | 433.3 |
| ±SD | 164.5 | 3.99 | 52.2 |

TABLE 7

MERSILENE TENSION to FAILURE RESULTS

| SPECIMEN | STIFFNESS [N/mm] | ULTIMATE DISPLACEMENT [mm] | ULTIMATE LOAD [N] |
|---|---|---|---|
| Mersilene 1 | 264.9 | 2.56 | 543.2 |
| Mersilene 2 | 273.6 | 2.39 | 541.5 |
| Mean | 269.3 | 2.48 | 542.4 |
| ±SD | 6.2 | 0.12 | 1.2 |

It will be appreciated by those skilled in the art that changes could be made to the embodiments described above without departing from the broad inventive concept thereof. It is to be understood, therefore, that this invention is not limited to the particular embodiment disclosed, but it is intended to cover modifications within the spirit and scope of the present invention as defined by the appended claims.

We claim:

1. A suture fixation device for securing tissue to bone comprising:
    a suture having:
        a plurality of slidable knots spaced apart from each other along a length of the suture, wherein each of the slidable knots are slidable towards a first knot position forming a securing knot; and
        a pouch wing formed by sliding the plurality of slidable knots towards the first knot position.

2. The suture fixation device of claim 1, further comprising growth factors infused within the suture.

3. The suture fixation device of claim 1, wherein the plurality of slidable knots comprise five knots.

4. The suture fixation device of claim 1, wherein the pouch wing includes at least one of platelet rich plasma and stem cells.

5. The suture fixation device of claim 1, wherein the suture includes a first suture fiber having a first color and the second suture fiber has a second color different from the first color.

6. The suture fixation device of claim 1, wherein the suture fiber is formed of an absorbable material.

7. The suture fixation device of claim 1, further comprising a square knot.

8. The suture fixation device of claim 1, wherein the suture comprises at least one of catgut, polyglycolic acid, polyglyconate, polydiaxone or polypropylene.

9. The suture fixation device of claim 1, wherein the suture fiber has a length of about 24 to 40 inches, and each of the plurality of slidable knots has an overall width of about 3.0 to 4.0 mm.

10. A method of securing tissue to bone comprising:
forming a through hole in a bone;
passing a first end of a suture fixation device through the through hole, the suture fixation device having a suture that includes a plurality of slidable knots spaced apart from each other and each slidable towards a first knot position;
securing the first end of the suture fixation device to tissue; and
forming a securing knot about a second end of the suture fixation device adjacent to the bone for applying tension to the tissue by sliding at least one of the plurality of slidable knots towards the first knot position.

11. The method of claim 10, wherein the securing knot has an overall width greater than an overall width of the through hole.

12. The method of claim 10, further comprising passing the suture fixation device through an eyelet.

13. A suture fixation device comprising:
a suture having:
growth factors infused within the suture;
a length of about 24 to 40 inches; and
a plurality of slidable knots spaced apart from each other along a length of the suture, wherein each of the plurality of slidable knots have an overall width of about 3.0 to 4.0 mm; and
a pouch wing formed by sliding the plurality of slidable knots towards a first knot position.

14. The suture fixation device of claim 13, wherein the pouch wing includes at least one of platelet rich plasma and stem cells.

15. The suture fixation device of claim 13, wherein the suture includes a first suture fiber having a first color and the second suture fiber has a second color different from the first color.

16. The suture fixation device of claim 13, wherein at least one of the plurality of knots comprises a square knot.

17. A method of securing tissue to bone comprising:
forming a through hole in a bone;
passing a first end of a suture fixation device having a plurality of knots spaced apart through the through hole;
securing the first end of the suture fixation device to tissue; and
forming a securing knot about a second end of the suture fixation device at a position along the length of the suture such that tension is applied to the tissue, wherein the securing knot has an overall width greater than an overall width of the through hole.

* * * * *